US010466164B2

(12) United States Patent
Ramlo et al.

(10) Patent No.: US 10,466,164 B2
(45) Date of Patent: Nov. 5, 2019

(54) SUSPENSION OF A SAMPLE ELEMENT WITH DIMENSIONAL STABILITY

(71) Applicant: Thermo Eberline LLC, Oakwood Village, OH (US)

(72) Inventors: Mark Jon Ramlo, Hudson Village, OH (US); Douglas B. Allen, Cuyahoga Falls, OH (US)

(73) Assignee: Thermo Eberline LLC, Oakwood Village, OH (US)

( * ) Notice: Subject to any disclaimer, the term of this patent is extended or adjusted under 35 U.S.C. 154(b) by 0 days.

(21) Appl. No.: 15/928,170

(22) Filed: Mar. 22, 2018

(65) Prior Publication Data

US 2018/0306700 A1   Oct. 25, 2018

Related U.S. Application Data

(60) Provisional application No. 62/489,614, filed on Apr. 25, 2017.

(51) Int. Cl.
*G01N 21/03* (2006.01)
*G01N 21/71* (2006.01)
(Continued)

(52) U.S. Cl.
CPC ............ *G01N 21/03* (2013.01); *G01N 21/64* (2013.01); *G01N 21/71* (2013.01)

(58) Field of Classification Search
CPC ........ G01N 21/03; G01N 21/64; G01N 21/71; G01T 1/10
See application file for complete search history.

(56) References Cited

U.S. PATENT DOCUMENTS 3,612,870 A   10/1971   Brennan
3,790,783 A   2/1974   Brunskill et al.
(Continued)

FOREIGN PATENT DOCUMENTS

GB   1480618 A   7/1977

OTHER PUBLICATIONS

Thermo Fisher: "Thermo Fisher Harshaw TLD Materials and Dosimeters," Jan. 1, 2016, retrieved from Internet (URL: https://assets.thermofisher.com/TFS-Assets/LSG/Catalogs/Dosimetry-Materials-Brochure.pdf) retrieved on Jun. 20, 2018.

*Primary Examiner* — Yara B Green
(74) *Attorney, Agent, or Firm* — William R. McCarthy (57) ABSTRACT

Substrates for suspending sample elements are disclosed, as well as sample platforms comprising such substrates, in which the sample elements can be analyzed with improved reliability. In exemplary embodiments, such sample elements are used in thermoluminescence dosimeters (TLDs) or optically stimulated luminescence dosimeters (OSLDs) to provide a calculated radiation dose with improved accuracy. The reproducibility associated with analyzing a sample element, and particularly one suspended by a film or encapsulated within films, may be significantly improved by tensioning the film(s). Tensioning may result during assembly of a sample platform, using a mechanical creasing force that is applied as the result of the configuration of a substrate of the sample platform, such as opposing sections or plates of this substrate. Alternatively, tensioning may be achieved using a separate application of force to the film(s) against a section or plate of the substrate.

18 Claims, 4 Drawing Sheets

(51) Int. Cl.
*G01N 21/64* (2006.01)
*G01T 1/10* (2006.01)

(56) References Cited

U.S. PATENT DOCUMENTS

| | | | | | |
|---|---|---|---|---|---|
| 3,894,238 | A | * | 7/1975 | Cox | G01T 1/02 |
| | | | | | 250/484.3 |
| 4,507,562 | A | | 3/1985 | Gasiot et al. | |
| 4,676,193 | A | * | 6/1987 | Martin | C23C 14/042 |
| | | | | | 118/504 |
| 4,825,084 | A | * | 4/1989 | Braunlich | G01T 1/11 |
| | | | | | 250/337 |
| 5,083,031 | A | * | 1/1992 | Hoelsher | G01T 1/11 |
| | | | | | 250/482.1 |

* cited by examiner

SUSPENSION OF A SAMPLE ELEMENT WITH DIMENSIONAL STABILITY

CROSS-REFERENCE TO RELATED APPLICATION

This application claims the priority benefit of U.S. provisional patent application Ser. No. 62/489,614 for "Suspension of a Sample Element with Dimensional Stability" by Mark Ramlo, filed Apr. 25, 2017, the entire disclosure of which is incorporated herein by reference.

FIELD OF THE INVENTION

The present invention relates to substrates used for suspending or holding sample elements, for example those comprising a material that emits electromagnetic radiation when exposed to heat (a thermoluminescent material) or to light (an optically stimulated luminescent material or radiophotoluminescent material). Exemplary substrates are those used in thermoluminescence dosimeters (TLDs) or optically stimulated luminescence dosimeters (OSLDs), in which the sample elements are read (e.g., exposed to a heat or light source) to emit electromagnetic radiation such as visible light or near ultraviolet light, in a quantity that relates to a radiation dose to which the sample element was subjected.

BACKGROUND OF THE INVENTION

Certain types of analytical equipment, which may be referred to generally as sample platforms, are used for suspending or holding sample elements, with one possible objective of allowing these sample elements to be analyzed (or "read") with as little signal contamination as possible from the surrounding substrate. Sample elements of particular interest exhibit luminescence, whereby materials such as minerals contained in these elements absorb energy upon irradiation that can be subsequently emitted, for example in the form of photons in the visible region of the electromagnetic spectrum. Thermoluminescence, in particular, is a form of luminescence in which electromagnetic radiation (normally visible light or near ultraviolet light) is emitted upon heating the sample element. Optically stimulated luminescence is another form of luminescence, in which electromagnetic radiation (also normally visible light or near ultraviolet light) is emitted upon exposing the sample element to light (e.g., having a wavelength that differs from that of the emitted electromagnetic radiation. The field of passive dosimetry is based on the use of these properties of some known materials to interact with ionizing radiation, the dose of which which can be later measured by using a reader to expose these materials to the appropriate energy form (e.g., heat or light at the appropriate temperature(s) or wavelength(s)) and measure the emitted light. Typical thermoluminescence dosimeters (TLDs) or optically stimulated luminescence dosimeters (OSLDs) are devices that include a substrate used to suspend or hold a sample element that exhibits thermoluminescence or optically stimulated luminescence, as the case may be. A dosimeter, such as a TLD or an OSLD, together with its respective reader and dose algorithm is referred to as a dosimetry system.

TLDs and OSLDs have developed significantly over the years, with the investigation into many types of materials exhibiting thermoluminescence and optically stimulated luminescence and their potential applicability to various areas of dosimetry. Such thermoluminescent and optically stimulated luminescent materials are capable of storing energy within their structure when irradiated, as electrons and holes become sequestered in "trapping centers" due to defects within the material. When the materials are exposed to heat (in the case of a thermoluminescent material) or to light (in the case of an optically stimulated luminescent material), electrons and holes recombine at "luminescence centers," causing the emission of electromagnetic radiation, typically visible light. A reader measures this electromagnetic radiation, e.g., photons emitted in the visible region that constitute the signal, using a PMT (photomultiplier tube), solid-state detector such as charge-coupled devices (CCDs), or similar light transducers inside the device. If, according to preferred luminescent materials, one photon is emitted from each trap center, the measured signal is an index of the number of electron/hole pairs and is proportional to the previously absorbed radiation dose.

TLDs and OSLDs are commonly used for personal radiation monitoring, for example of those who may be exposed to radiation of greater than 3/10 of the dose equivalent limits. Monitoring in some settings, such as in the remediation of nuclear power plant accidents or in research laboratories investigating radiochemical applications, is considered essential to ensure compliance with maximum permissible dose standards. To this end, TLDs and OSLDs may employ multiple types of sample elements to more comprehensively determine doses received by an individual at specific depths within, and areas of, the body. For example, doses may be measured (1) at 10 mm to the whole body (Hp(10)), (2) at 3 mm to the lens of the eye (Hp(3)), and/or (3) at 0.07 mm to the extremities (Hp(0.07)). Applications for TLDs and OSLDs extend to environmental, neutron, and clinical monitoring, with commercially significant uses being in radiotherapy for cancer treatment, diagnostic radiation measurements, the dating of materials, and the analysis of meteorites.

Improvements in TLDs and OSLDs and, more generally, any types of substrates and associated sample platforms for suspending or holding sample elements that can be analyzed or read (by exposure to an appropriate energy source) in a reliable manner, are continually being sought.

SUMMARY

Aspects of the invention are associated with the discovery of substrates for suspending or holding sample elements, as well as sample platforms comprising such substrates, in which the sample elements can be analyzed with improved reliability. In exemplary embodiments, such sample elements are used in dosimeters (e.g., TLDs or OSLDs) to provide a calculated radiation dose with improved accuracy and/or repeatability. A sample element may, according to particular embodiments, be suspended by a film such as a plastic layer or multi-layer plastic laminate, and in some cases the sample element may be encapsulated between two films or laminates. Particular aspects of the invention relate to the discovery that such films may be prone to unpredictable movements during analysis or reading of a given sample element, for example upon its exposure to a source of energy (e.g., exposure to heat at an appropriate time-temperature profile or exposure to light at an appropriate wavelength) in a reader of a dosimetry system, as described above. These movements, in turn, can adversely affect the measurements of the light collection optics, such as the PMT, solid-state detector, or other light transducer described above, resulting in unacceptable reproducibility of a dosimetry system or other system in which a suspended sample element is analyzed or read.

Surprisingly, it has now been discovered that the reproducibility and/or repeatability associated with analyzing a sample element, and particularly a sample element suspended or held by a film, such as encapsulated within films (e.g., in either case within an opening of a substrate), may be significantly improved if the film is tensioned during assembly of the sample platform (for example by increasing film tension during assembly, relative to a non-tensioned or relaxed state, or alternatively relative to a pre-tensioned state). The term "tensioning" may refer to the application of force to (something) that tends to stretch it. The tensioned state of a film can, for example, be compared to the film in a non-tensioned or relaxed state, i.e., a state where no stretching force has been applied. Tensioning may be achieved using a mechanical creasing force that is applied to the film(s) as the result of the configuration of a substrate of the sample platform (e.g., opposing sections or plates of this substrate), or otherwise as the result of a separate application of force to the film(s) against a section or plate of the substrate. This separate application may occur prior to aligning of an opposing section or plate of the substrate to secure or sandwich the film between the sections or plates.

Whether tensioning of the film (e.g., a central region of the film that extends across a substrate opening) is achieved by the configuration of the substrate or by a separate application of force (or both) as described above, those skilled in the art with knowledge gained from the present specification will appreciate that the tension of the film(s) may be advantageously increased during preparation (assembly) of the sample platform, comprising a substrate and sample element suspended by a central region of the film(s) within an opening of the substrate. That is, such preparation can comprise (1) affixing an outer region of the film(s) to a first section or first plate of the substrate, such that the central film region(s), which support the sample element, extend across a first section opening or a first plate opening, and (2) aligning a second section opening or a second plate opening (of a second section or a second plate) with the first section opening or first plate opening to form a substrate opening. An initial tension of the central region of the film(s), namely a tension with which at least one of the film(s) is affixed in step (1) to extend across the first section or plate opening, may be increased following the aligning in step (2) of the second section opening or second plate opening to form the sample platform. Accordingly, the central region of the film(s) of a representative sample platform may have a final tension that is greater than the initial tension of the central region of the film(s), as affixed initially to the first section opening or first plate opening. This increase in tension may be relative to an initial tension that is representative of a non-tensioned or relaxed state of the film, as described above. Alternatively, this increase in tension may be relative to an initial tension that is representative of a pre-tensioned state of the film, in which some stretching force has been applied, but at an initial tension that is nonetheless less than the final tension of the central region of the film(s) in the sample platform as assembled.

The improvements in analytical measurement performance, resulting from tensioning of the film (e.g., to achieve a final tension as described above), can be attributed to a reduction in a significant portion (e.g., over 50%) of the otherwise allowable (e.g., in the case of a conventional, non-tensioned film) movement of the sample element during analysis. In subjective terms, extensive studies have revealed that, in the absence of film tensioning, sample elements described herein have a propensity, during their exposure to heat, light, or other source of energy that accompanies their analysis, to move up, twist, or move down. In turn, even small sample movements have, in these studies, been experimentally correlated to significantly reduced reliability (such as in terms of reproducibility and/or repeatability) in the analysis or reading of the sample elements (e.g., to determine a radiation dose). Overall, the improvements associated with tensioning have significant commercial implications, particularly in view of the increasing demand for dosimetry systems, coupled with their industrial performance requirements.

Embodiments of the invention are directed to a substrate for suspending or holding a sample element, wherein top and bottom sections of the substrate are configured to mechanically tension a central region of a film, for suspending a sample element, across a substrate opening formed by these sections. In exemplary embodiments, the sample element may be encapsulated within two films, e.g., a supporting film and a covering film, both of which are tensioned as described herein. According to particular embodiments, the top and bottom sections of the substrate are configured to provide a final tension of the central region of the film that exceeds (is increased relative to) an initial tension with which the film is affixed to either the top or bottom section.

Further embodiments are directed to a sample platform, such as a dosimetry card, comprising a substrate as described above, in addition to a sample element suspended or held by a central region of a film, or, according to more particular embodiments, encapsulated between central regions of supporting and covering films, within a substrate opening. According to particular embodiments, the central region of the film has a final tension in the sample platform that exceeds an initial tension as described above.

Yet further embodiments are directed to a method for determining a radiation dose, comprising reading the sample element that is suspended or held in the opening of the sample platform as described above. Reading may be performed by exposure of the sample element to heat (in the case of a sample element comprising a thermoluminescent compound) or to light (in the case of a sample element comprising an optically stimulated luminescent compound). In the first case, the method may comprise, in particular, heating the sample element according to a time-temperature profile and measuring the intensity of electromagnetic radiation such as visible light or near ultraviolet light, emitted by the sample element during the heating, such as during a particular acquisition period of the heating. In the second case, the method may comprise exposing the sample element to light, with the light used for stimulation of the sample element possibly having a first wavelength that differs from a second wavelength of the electromagnetic radiation emitted by the sample element during the acquisition period. For example, the light used for stimulation of the sample element and the electromagnetic radiation may both be visible light, but having different wavelengths (e.g., green light may be used for stimulation, whereas blue light may be emitted and its intensity measured as the basis for determining a radiation dose). In the case of the electromagnetic radiation emitted from sample elements comprising luminescent compounds, representative wavelengths of such electromagnetic radiation are generally from about 200 nanometers (nm) to about 700 nm, and more typically from about 300 nm to about 550 nm, representative of visible light or near ultraviolet light.

According to any of the methods described herein for determining a radiation dose, such methods may further comprise correlating the measured intensity, emitted by the sample element during the acquisition period, with the radiation dose. Advantages of these methods, particularly with respect to reduced movement of the sample element and the associated, increased reproducibility and/or repeatability over multiple radiation dose determinations, are described in greater detail below.

Still further embodiments are directed to a method of making a dosimeter card (e.g., a TLD card or an OSLD card), comprising (i) affixing an outer region of a film to a first plate of a substrate, in a manner such that a central region of the film, which supports or holds a sample element, extends across a first plate opening and (ii) aligning a second plate opening of a second plate with the first plate opening to form a substrate opening. The film may be tensioned across the substrate opening by a crease formed in the film at an edge of the substrate opening. Tensioning may, in particular, be performed by creasing the film against the first plate of the substrate, for example at a lower corner edge of the first plate at the first plate opening. Such creasing may be a separate step, prior to aligning the second plate opening with the first plate opening. The creasing may also be performed "automatically" as the result of a configuration of the first and second plates upon their alignment to form the substrate opening, for example a configuration in which an extension element of the second plate protrudes radially inward to a greater extent, relative to the first plate opening. Such an extension element may be angled, relative the plane of the substrate opening. In the case of an angled extension element, the first and second plates, upon their alignment, may provide the substrate opening with a chamfer or bevel. As described above, according to particular embodiments, a final tension of the central region of the film, achieved upon aligning of the second plate in step (ii) may advantageously exceed an initial tension with which the film is affixed in step (i).

These and other embodiments will become apparent from the following detailed description.

The figures should be understood to present illustrations of embodiments of the invention and/or principles involved. As would be apparent to one of skill in the art having knowledge of the present disclosure, other devices, methods, and particularly equipment used in dosimetry, such as dosimetry cards, will have configurations and components determined, in part, by their specific use. Like reference numerals refer to corresponding parts throughout the several views of the drawings.

DETAILED DESCRIPTION OF EMBODIMENTS

Terms that designate a particular spatial orientation or direction, such as "up," "down," "upward," "downward," "top," "bottom," and "lower," are used for ease of understanding and particularly for indicating positions of certain elements relative to other elements. These terms may also refer to preferred orientations of elements, when positioned in a dosimetry card reader. However, these terms do not limit the substrates and sample platforms, described herein, to particular spatial orientations. The interchangeability, for example, of "a top substrate section" with "a bottom substrate section" would be understood by those skilled in the art, particularly in view of the possible substitutions of elements described herein, such as the substitution of "top substrate section" and "bottom substrate section" with "first plate" and "second plate," respectively.

The term "light," particularly in the context of light that is used for reading of a sample element comprising an optically stimulated luminescent compound, i.e., the light to which such a sample element is exposed to cause emission of electromagnetic radiation, refers to electromagnetic radiation generally and is not limited to "visible light," which refers more specifically to electromagnetic radiation in the visible portion of the electromagnetic spectrum. Therefore, the term "light" can refer, for example, to radio waves that are used to stimulate a radio-photoluminescent material. Use of the term "light" is therefore principally to distinguish electromagnetic radiation used for stimulating a luminescent material, as opposed to electromagnetic radiation that is emitted from such material, for example during reading as described herein.

The term "reading" refers to the exposure of a sample element to any type of energy, including heat, light, sound, vibration, etc. that allows for the acquisition of information from the sample element, such as a radiation dose to which the sample element was subjected (e.g., during a period of ionizing radiation exposure of a subject in close proximity to the sample element). "Reading" may more particularly refer to exposure of a sample element comprising a thermoluminescent compound to a source of heat (e.g., an electrically resistive element), or to exposure of a sample element comprising an optically stimulated luminescent compound to a source of light (e.g., from a lamp). As described herein, aspects of the invention are associated with improvements in dimensional stability of a sample element during reading, leading to corresponding improvements in measuring the desired information from the sample element.

As noted above, embodiments of the invention relate to substrates for suspending or holding sample elements. Combinations of these substrates and sample elements, together with films used to suspend or hold (e.g., encapsulate) the sample elements across substrate openings, may be referred to as sample platforms. Such sample platforms, according to specific embodiments, may be used as thermoluminescence dosimeters (TLDs) and referred to as TLD cards; used as optically stimulated luminescence dosimeters (OSLDs), and referred to as OSLD cards; or used as radio-photoluminescence dosimeters (RPLDs), and referred to as RPLD cards. By virtue of tension being applied to one or more films used to suspend or hold a sample element (e.g., encapsulate the sample element between two films), substrates and sample platforms described herein advantageously improve positional stability (i.e., reduce upward, downward, and/or twisting movement) of the sample element, particularly when heated or exposed to light or other form of energy, during analysis or reading of the sample element. Such tension may be applied according to the manner in which the substrates, or parts thereof, are mechanically configured. Alternatively, the tension may result from a separate (e.g., manual) application of force during assembly of the sample platform. In either case, the associated improvement in stability has been shown to greatly increase analytical reproducibility and therefore overall quality of the sample platforms. This, in turn, provides significant benefits to the users of such sample platforms, including users of dosimetry cards who are exposed, or are at risk of exposure, to ionizing radiation. As described above, the application of tension, or "tensioning" may refer to increasing of the tension of a central region of the one or more films, relative to an initial tension with which the film is initially applied or affixed to a section or plate of the substrate, prior to aligning or adjoining of that section or plate to an abutting, second section or plate.

Figure 1:
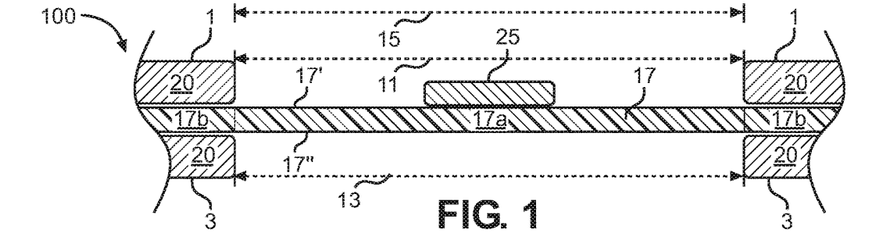
FIG. 1 illustrates a side, cut-out view of a portion of a conventional sample platform such as a dosimetry card.

FIG. 1 illustrates a side view of a portion of a conventional sample platform 100 such as a dosimetry card. The platform includes a substrate 20, with top and bottom substrate sections 1, 3, which may be in the form of top and bottom substrate plates. These sections 1, 3 are configured, upon alignment of a top section opening 11 with a bottom section opening 13, to form an opening through the substrate, e.g., substrate opening 15, which may have substantially the same opening size (e.g., diameter in the case of a circular substrate opening) as both top section opening 11 and bottom section opening 13. The shape of substrate opening 15 may vary and is not critical to the practice of the present invention. Representative substrate openings may be circular, oval, or polygonal (e.g., rectangular, such as square). As is further illustrated in FIG. 1, a central region 17a of a film 17 extends across substrate opening 15, whereas top and bottom substrate sections 1, 3 are configured, upon alignment, to engage an outer region 17b of film 17, external to central region 17a. This engagement at outer region 17b is achieved by contact with top and bottom substrate sections 1, 3 and particularly at respective, top and bottom faces 17', 17'', of film 17. That is, top and bottom substrate sections 1, 3, may be said to overlay, clamp, or sandwich film 17 at outer region 17b.

Central region 17a of film 17 therefore extends across substrate opening 15, and, as further illustrated in FIG. 1, suspends or holds sample element 25 within the opening 15. Sample element 25 may be in the form of a flat disk having a cross-sectional shape that is the same as, or different from, the shape of substrate opening 15 as described above. As with substrate opening 15, sample element 25 may have a circular, oval, or polygonal (e.g., rectangular, such as square) cross-sectional shape, with the exact geometry not being a critical feature of the invention. More relevant is the ability of substrate opening 15 to have sufficient size to encompass sample element 25 and provide sufficient space between sample element 25 and substrate sections 1, 3 such that, upon analysis or reading of sample element (e.g., using a TLD card reader or OSLD card reader), signal contamination from substrate sections 1, 3 is minimal or negligible. Those skilled in the art will appreciate suitable geometries and dimensions of substrate opening 15 and sample element 25. According to a particular embodiment, substrate opening 15 is circular and the cross-sectional shape of sample element 25 is also circular and substantially concentric with, but having a smaller diameter relative to, substrate opening 15.

Sample element 25, in the case of its use in TLD, may comprise a thermoluminescent compound, such as lithium fluoride (LiF), lithium borate ($Li_2B_4O_7$), beryllium oxide (BeO), magnesium borate ($MgB_4O_7$), calcium sulfate ($CaSO_4$), calcium fluoride ($CaF_2$), aluminum oxide ($Al_2O_3$), or magnesium orthosilicate ($Mg_2SiO_4$). According to specific applications involving radiation dose monitoring to human or animal tissue, sample element 25 may comprise lithium fluoride doped with a doping element selected from the group consisting of magnesium, titanium, copper, phosphorous, silver, dysprosium, thulium, and combinations thereof, with particular examples of doped thermoluminescent compounds being LiF:Mg,Ti and LiF:Mg,Cu,P. Other examples for such applications include calcium fluoride doped with dysprosium or manganese ($CaF_2$:Dy or $CaF_2$:Mn). Sample element 25 may alternatively comprise an optically stimulated luminescent compound, such as carbon-doped aluminum oxide ($Al_2O_3$:C), europium ion-doped rubidium magnesium fluoride ($RbMgF_3$:$Eu^{+2}$), or a radio-photoluminescent material, such as silver-activated phosphate glass.

Figure 2:
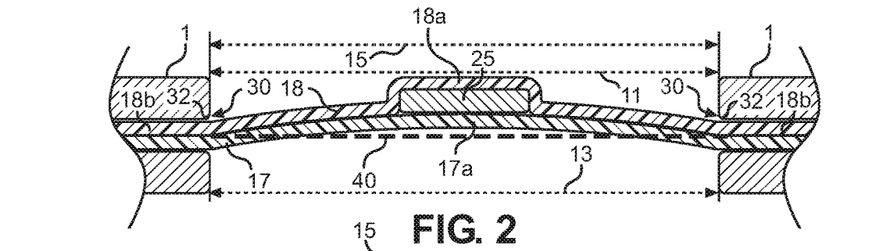
FIG. 2 illustrates a side, cut-out view of a portion of a sample platform, in which a film is tensioned across a substrate opening, by creasing the film at the edge of the opening, against a top plate of the substrate of the sample platform.

Film 17 or films 17, 18 (in the case of a second film 18 being used) are generally transparent, or at least translucent, plastic materials, having representative thicknesses generally from about 0.5 to about 10 mils (about 0.013 mm to about 0.25 mm), typically from about 1 to about 5 mils (about 0.025 mm to about 0.13 mm), and often from about 1.5 mils to about 2.5 mils (about 0.038 mm to about 0.64 mm). Such thicknesses may be obtained using a single layer or ply, or otherwise multiple layers or plies (e.g., 2 or more plies). In the case of using film(s) to suspend or encapsulate a sample element comprising a thermoluminescent compound, film(s) are preferably also heat resistant materials, having a melting temperature greater than that to which sample element 25 is to be heated, for example according to a predetermined protocol. A representative protocol is a time-temperature profile (TTP) that is used to resolve a glow curve of the sample, in the determination of an associated radiation dose. For such heating applications, the film(s) may have a melting point exceeding 300° C. Representative film(s) useful in any of the embodiments described herein, may, for example, comprise a fluoropolymer such as polytetrafluoroethylene (e.g., Teflon®) or a polyimide (e.g., Kapton®). According to a particular embodiment in which films 17, 18 are used to encapsulate sample element 25, such films may be bonded through the application of pressure and/or heat about the periphery of the sample element. Representative films having suitable properties include unsintered, non-directional extruded films. Alternatively, films 17, 18 may be bonded through the use of an adhesive. Directional films, such as machine direction orientation (MDO) films or transverse direction orientation (TDO) films may also be used. Temperature stability of the film(s) may be improved by cross-linking. Preferably, the film(s) are transparent to visible light. Likewise, sample element 25 may also include a heat resistant material (e.g., a fluoropolymer such as polytetrafluoroethylene), acting as a carrier of the luminescent compound (e.g., thermoluminescent compound or optically stimulated luminescent compound) and, according to particular embodiments, having the luminescent compound dispersed uniformly therein at a desired concentration.

FIG. 2 illustrates film 17 being tensioned by the formation of a crease 30, for example by the application of upward mechanical or manual force to film 17 against top section 1 of substrate 20, which mechanical or manual force may be applied more specifically at lower corner edge 32 of top substrate section 1, at top section opening 11. FIG. 2 further illustrates, in addition to use of film 17 below sample element 25 that may be considered a supporting film, a second film 18 above sample element 25 that may be considered a covering film. In this manner, according to the embodiment of FIG. 2, sample element 25 may be suspended or held by central region 17*a* of film 17 as illustrated in FIG. 1, or may otherwise be encapsulated between central regions 17*a*, 18*a* of film 17 and second film 18, which serve as supporting and covering films, respectively. Outer regions of 17*b*, 18*b* of film 17 and second film 18 may refer to those regions external to respective central regions 17*a*, 18*a* that are engaged by contact with top and bottom substrate sections 1, 3, as shown in FIG. 2. According to the embodiment illustrated in FIG. 3, second film 18 includes only a central region 18*a* thereof, sufficient to cover sample element and encapsulate it between film 17 and second film 18. Although not illustrated in FIGS. 4 and 5 for ease of explanation, second film 18, serving as a covering film for sample element 25, may be used, in the same manner illustrated in FIGS. 2 and 3, likewise in the embodiments depicted in FIGS. 4 and 5.

As shown in FIG. 2, as a result of the formation of a crease 30 to tension film 17 (as well as second film 18), this film is displaced, in this case in an upward direction, such that film 17 is offset in its central region 17*a* from a plane 40 of substrate opening 15, i.e., a plane parallel to, and disposed centrally with respect to, top and bottom substrate sections 1, 3. Due to tensioning, which results in this displacement or bending of film 17 (as well as film 18, if used) and consequently sample element 25, the sample element is positionally stabilized, such that its potential movement, such as during heating, or otherwise during exposure to light or other source of energy, as needed to read the sample element and determine a radiation dose, is significantly reduced. This improved positional stability, in the case of sample element 25 being suspended or held on tensioned film 17, or otherwise being encapsulated between tensioned film 17 and second film 18 (which second film may or may not be tensioned), has been found to be associated with the important advantages described above.

Figure 3:
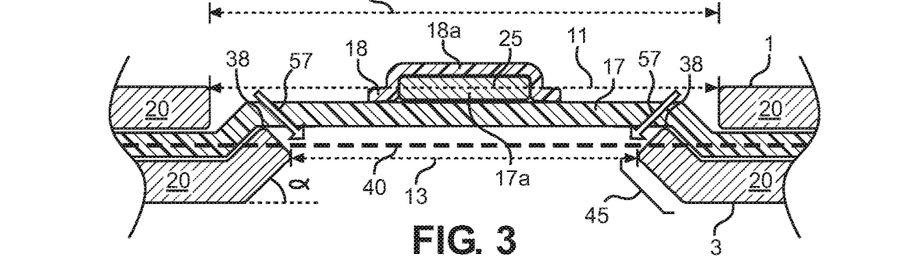
FIG. 3 illustrates a second embodiment according to which a film is tensioned across a substrate opening, but with the creasing of the film against the top plate resulting from a modified configuration of the bottom plate.
Figure 4:
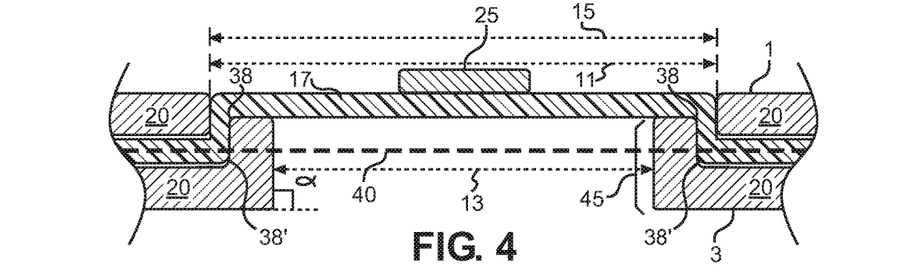
FIG. 4 illustrates a third embodiment according to which a film is tensioned across a substrate opening, but with the modified configuration of the bottom plate including an extension element having a different angle, compared to that shown in FIG. 3.

As illustrated in FIG. 3, the top and bottom substrate sections 1, 3 themselves are advantageously configured, e.g., upon alignment of their respective openings 11, 13 (as described above with reference to FIG. 1), to mechanically tension central region 17*a* of film 17 across substrate opening 15. As in the embodiment illustrated in FIG. 2, film 17 is again displaced, such that it is offset in central region 17*a* from (e.g., central region 17*a* is above) plane 40 of substrate opening 15. The displacement or bending occurs along an edge 38 or periphery of substrate opening 15, and in this case edge 38 being formed at least in part by an extension element 45 of bottom substrate section 3. As shown, extension element 45 extends beyond the periphery of top substrate section 1, or protrudes radially inward, into top section opening 11. Stated otherwise, extension element 45 of bottom substrate section 3 extends into substrate opening 15 to a greater extent, relative to top substrate section 1. Accordingly, in the embodiment of FIG. 3, as well as in the embodiment of FIG. 4, bottom section opening 13 is narrowed, relative to top section opening 11, such that alignment of these openings may in this case more specifically refer to alignment (such as vertical or co-axial alignment) of respective centers of these openings (e.g., such that circular openings in the top and bottom substrate sections 1, 3 are concentric). In addition, the substrate opening 15 in this case may be designated as corresponding in size to the opening in that substrate section (1 or 3) having the larger diameter or otherwise the larger dimension, in the case of non-circular openings. Therefore, in the embodiment of FIG. 3, as well as in the embodiment of FIG. 4, the substrate opening 15 may be designated as corresponding in size to top section opening 11.

Figure 5:
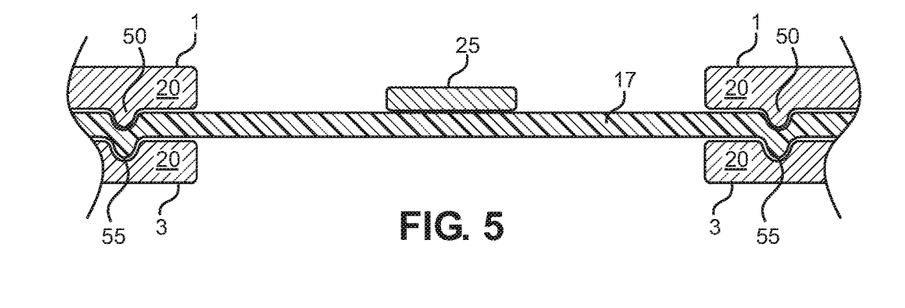
FIG. 5 illustrates a fourth embodiment, according to which a film is tensioned across a substrate opening, using modified configurations of both the top plate and the bottom plate.

As further shown in FIG. 3, extension element 45 of bottom substrate section 3 is angled, and in particular in a direction, as dictated by a non-zero value of angle $\alpha$, that is offset from the direction of plane 40 of substrate opening 15, as described above. A representative angle $\alpha$ is 45°, although generally angles within the range of 10-80° are suitable, as well as other angles. Due to angled extension element 45 in the embodiment of FIG. 3, the alignment of top and bottom substrate sections 1, 3 to form substrate opening 15, may provide a chamfer or bevel 57. According to FIG. 4, the angle of extension element 45 is increased to 90°. As shown in this embodiment, and as applicable generally to any of the angled extension elements described herein, edge 38, which is used to cause upward displacement of central region 17*a* of film, may be rounded. Other edges, such as second edge 38', of angled extension element 45, may similarly be rounded, in order to alleviate localized stresses on film 17. FIG. 5 illustrates yet a further embodiment, in which tensioning of film 17 occurs through the use of a mating protrusion or bead 50 in top substrate section 1 that aligns with a corresponding recession or groove 55 in bottom substrate section 3, such that when sections 1, 3 are aligned to form substrate opening 15, film 17 is pulled into groove 55 with the desired result of mechanical tensioning.

Figure 6A:
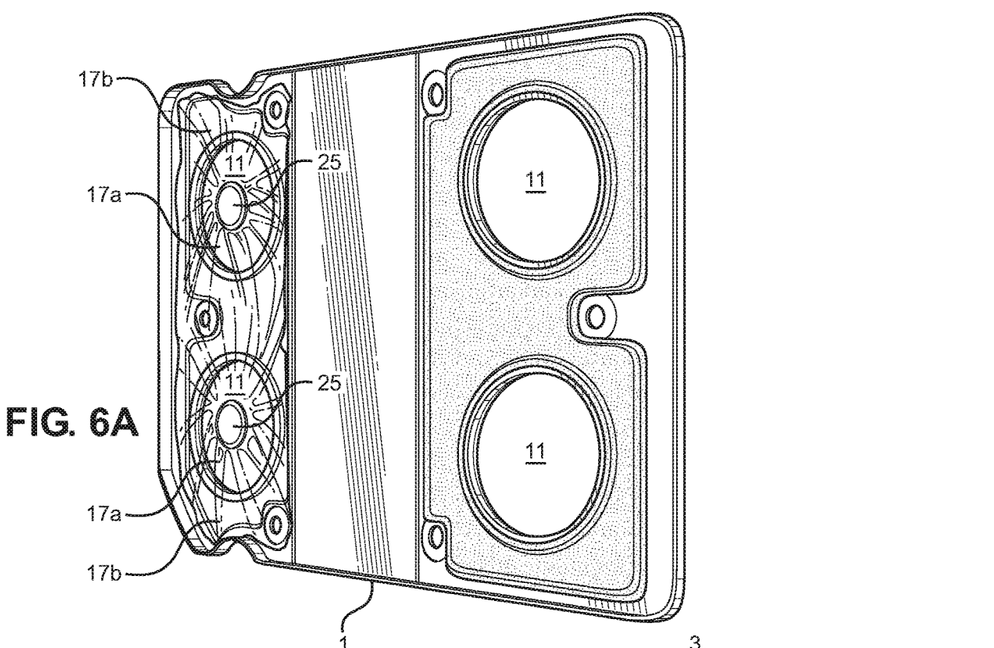
FIGS. 6A and 6B illustrate, respectively, overhead views of top and bottom sections of a substrate, with a film being affixed to the top substrate section, and with a central region of the film supporting sample elements being suspended or held within top section openings.
Figure 6B:
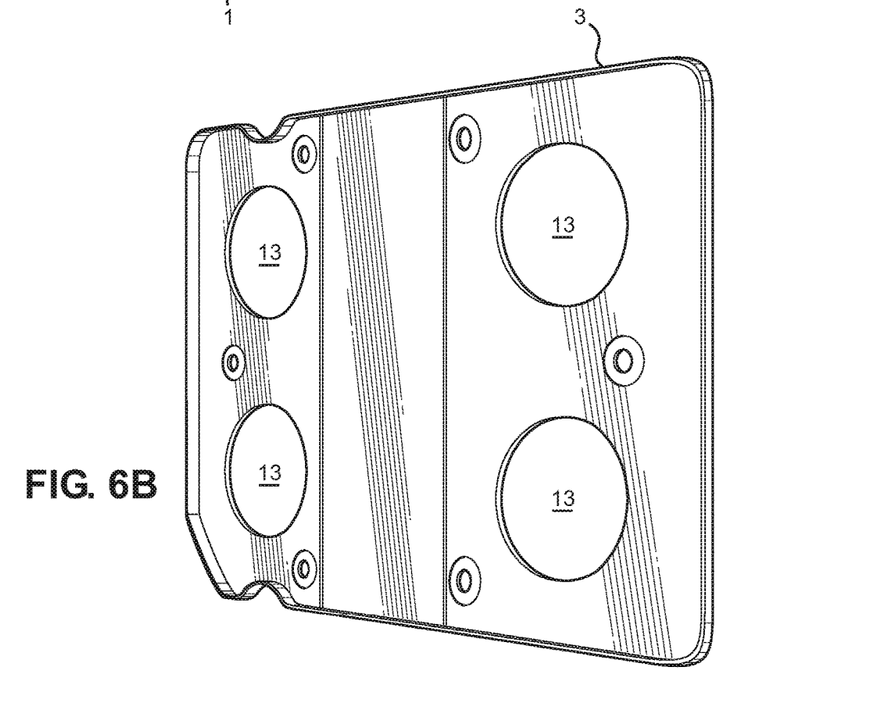

FIGS. 6A and 6B provide alternative views of the top substrate section (or first plate) 1 and bottom substrate section (or second plate) 3 that align to form substrate 20 as shown in FIGS. 1-5. In particular, these figures illustrate elements of a sample platform, such as the dosimeter card 200, which may be a thermoluminescence dosimeter (TLD) card or an optically stimulated dosimeter (OSLD) card, as shown in assembled form in FIG. 7. In representative methods for the assembly of, or for making, a sample platform, outer region 17*b* of film 17 may be affixed to the top substrate section, or first plate 1, of the substrate, in a manner such that central region 17*a*, which supports, holds, or at least partly encapsulates sample element 25, extends across top section opening, or first plate opening 11. FIG. 6A, showing first plate 1, illustrates central regions 17*a* of film 17 extending across two first plate openings 11, whereas two other first plate openings 11 are shown uncovered by film 17. At least one bottom substrate section opening, or second plate opening 13, of the second plate 3 may be aligned with at least one first plate opening 11 to form substrate opening 15, as depicted, for example, in FIG. 2. The film may be tensioned across substrate opening 15, by creasing the film at an edge of substrate opening 15. According to a particular embodiment, film 17 may be tensioned by creasing it against first plate 1, for example at lower corner edge 32 (as depicted with respect to top substrate section 1 in FIG. 2) of first plate 1 at first plate opening 11, prior to the aligning second plate opening 13 with first plate opening 11. According to another particular embodiment, creasing may be performed upon the aligning of the second plate 3, by an extension element 45 of this plate (as described above and depicted with respect to bottom substrate section 3 in FIGS. 3 and 4), which extends or protrudes radially inward, into first plate opening 11. Stated otherwise, this extension element 45 of the second plate 3 extends into substrate opening 15 to a greater extent, relative to first plate 1.

Figure 7:
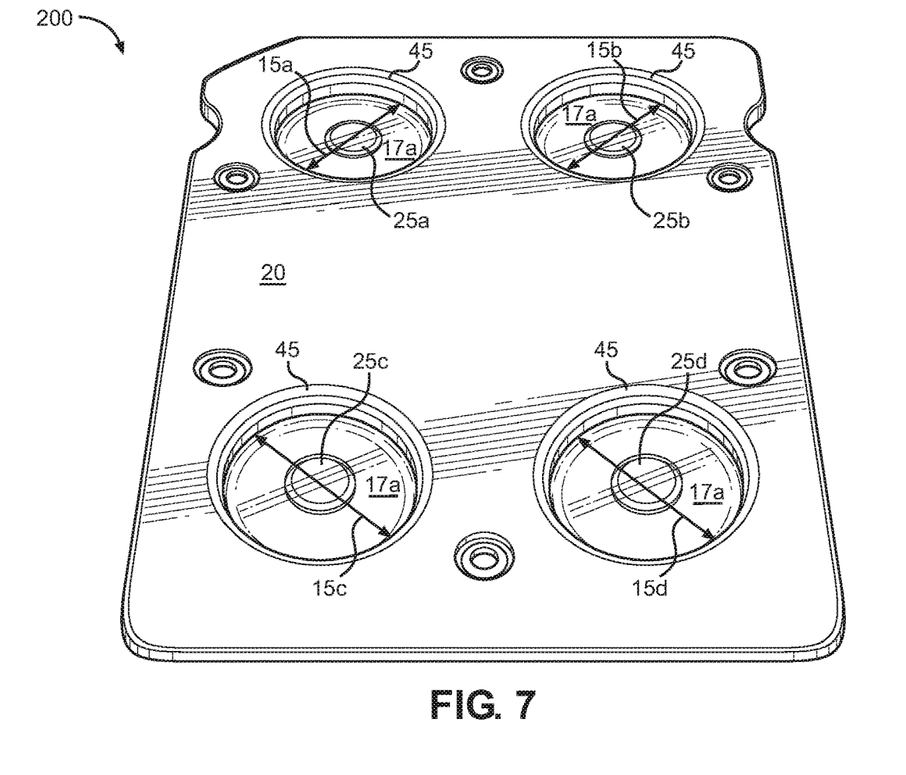
FIG. 7 illustrates a sample platform, following alignment of the top and bottom sections of the substrate, as depicted in FIGS. 6A and 6B, with the sample platform including the film and suspended sample elements.

Accordingly, FIGS. 6A and 6B illustrate components of a sample platform or dosimeter card 200 as depicted in FIG. 7 and comprising a substrate 20 having an opening 15a across which a central region 17a of a film extends. As further shown in FIG. 7, the sample platform further comprises a sample element 25a suspended or held by this central region 17a, within opening 15a. As depicted in FIGS. 2 and 3, sample element 25a may also be enclosed or encapsulated between the film 17 (e.g., a bottom film) and a second film 18 (e.g., a top or covering film) that likewise may extend across opening 15 (FIG. 2) or otherwise may be applied locally over sample element 25a (FIG. 3), without extending across opening 15. Central region 17a of the film may be tensioned across opening 15a according to any manner described herein, including as depicted in the particular embodiments illustrated in FIGS. 2-5, to reduce movement of the sample element upon reading, as described herein.

As is more particularly illustrated in FIG. 7, the substrate 20 of the sample platform 200 may comprise one or more further openings 15b, 15c, 15d across which one or more further central regions 17a of the film extend, or possibly across which further central regions 17a, 18a of both first and second, sample element encapsulating films 17, 18 extend, as illustrated in greater detail in FIGS. 2 and 3. Accordingly, the sample platform may further comprise one or more further sample elements 25b, 25c, 25d suspended or held by respective one or more further central regions 17a within the respective one or more further openings 15b, 15c, 15d. It may be additionally appreciated that central regions 17a of a single film of a sample platform may be within different openings 15a-d, or otherwise separate film pieces may be within these different openings, with such film pieces nonetheless being overlayed, clamped, or sandwiched by first and second substrate plates 1, 3, as shown in FIGS. 6A and 6B. Each of the further central regions 17a of the film(s), or at least a subset of such regions, is tensioned across respective one or more further openings 15b, 15c, 15d, according to any manner described herein, including as depicted in the particular embodiments illustrated in FIGS. 2-5, to reduce movement of the sample element(s) upon reading.

In the particular embodiment of FIG. 7, substrate 20 comprises four openings 15a-d, each of which having suspended or held therein a respective sample element 25a-d. Each of these four sample elements 25a-d may comprise a different luminescent material type (e.g., selected from the doped compounds as described above) and/or material mass density, for measuring or monitoring differing types of ionizing radiation. For example, a first sample element may be used to monitor radiation received at the eye/lens level (Hp(3)), a second sample element may be used to monitor radiation received at the internal organ level (Hp(10)), a third sample element may be used to monitor radiation received at the skin/extremity level (Hp(0.07)), and a fourth sample element may be used to monitor radiation received in the form of neutrons having an intermediate level of penetration. In the sample platform 200 illustrated in FIG. 7, central region(s) 17a of the film or otherwise separate films may be tensioned across any of their respective openings in any manner described herein, including by displacement of the film(s) in a direction that is offset from planes of the respective openings, as described above. Displacement may occur, for example, along respective edges of these openings and may, in particular, result from creases in the film(s) at the edges of the respective openings. As described above, the film(s) may be tensioned specifically by creasing the film against the first plate of the substrate, such as at a lower corner edge of the first plate at the first plate opening, prior to the aligning of the second plate opening with the first plate opening. Creases in the film(s) may otherwise be formed upon alignment of the first plate of the substrate with the second plate of the substrate having an extension element, such as an angled extension element described above. This angled extension element may protrude radially inward into a respective substrate opening, to provide a chamfer or bevel in this opening. In exemplary embodiments, openings 15a-d are each circular with diameters ranging generally from about 5 millimeters (mm) to about 75 mm, and typically from about 10 mm to about 30 mm. In other exemplary embodiments, sample elements 25a-d are circular with diameters ranging generally from about 3 mm to about 50 mm, and typically from about 5 mm to about 35 mm.

Sample platforms, such as dosimetry cards as described herein, may be used in conjunction with readers in dosimetry systems that allow the determination of a radiation dose received by sample element(s) of these platforms or cards. Representative embodiments of the invention are therefore directed to a method for determining a radiation dose, comprising reading a sample element suspended or held (e.g., encapsulated) in the opening of the sample platform as described above, for example in a dosimetry card reader. The reading of the sample element may comprise exposing it to heat, for example according to a predetermined time-temperature profile (TTP). The TTP may include at least a thermoluminescence dosimetry (TLD) acquisition period at an elevated temperature, for example generally between about 150° C. and about 400° C., and typically between about 300° C. and about 400° C. The reading of the sample element may alternatively comprise exposing it to light of an appropriate, stimulatory wavelength during an optically stimulated luminescence dosimetry (OSLD) acquisition period. In either case, the method may include measuring the intensity of electromagnetic radiation such as visible light or near ultraviolet light, emitted by the sample element during at least the acquisition period. The method may also include correlating the intensity, measured during this acquisition period, with the radiation dose.

According to a representative method, movement of the sample element may be reduced, relative to a reference method with all parameters being the same, but with the reference method excluding tensioning of the film as described herein. These same parameters include (i) the sample platform and its components, including the substrate, sample element, and film as described above, and the configuration of these components, and (ii) the energy (e.g., the time-temperature profile, the light, or other form of energy) to which the sample platform is subjected, during reading of the sample element. According to other embodiments, the method may provide increased reproducibility (i.e., a decrease in variation over multiple radiation dose determinations for a sample element having received the same radiation dose), relative to the reproducibility of a reference method for determining a radiation dose with all parameters being the same, including parameters (i) and (ii) above, as well as the type(s) and amount(s) of ionizing radiation received by the sample element, prior to performing the method.

Figure 8:
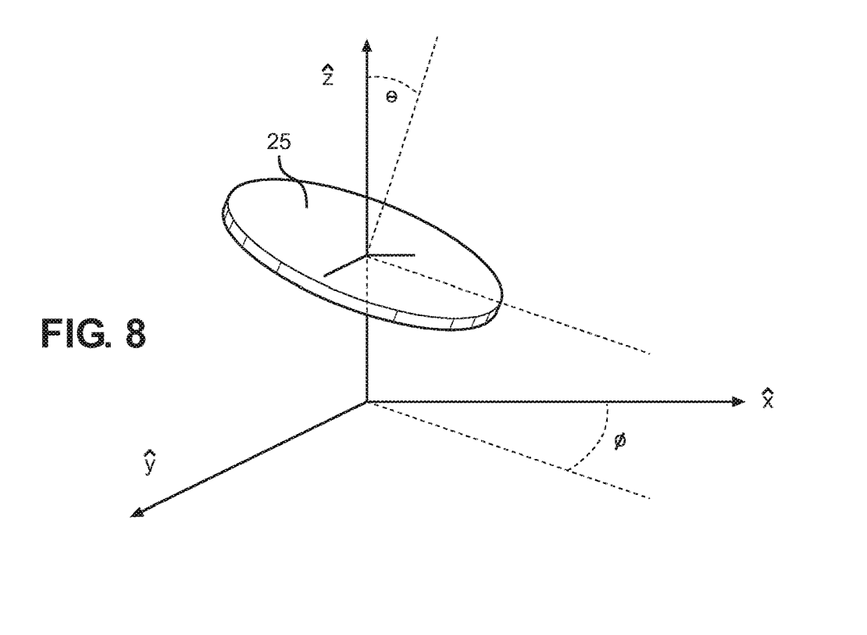
FIG. 8 illustrates possible movements of a sample element that is suspended by a film or encapsulated between two films.

FIG. 8 illustrates various possible movements of sample element 25 during reading to ascertain a radiation dose, for example by heating according to a time-temperature profile or by exposure to light of a stimulatory wavelength. These include movements upward or downward (z-direction) as well as twisting movements (θ-direction and ø-direction). By virtue of upward displacement of a central region of the film that suspends, for example encapsulates, the sample element as described above, the movement of the sample element that is reduced during reading, may be a downward movement or a twisting movement of the sample element.

Figure 9:
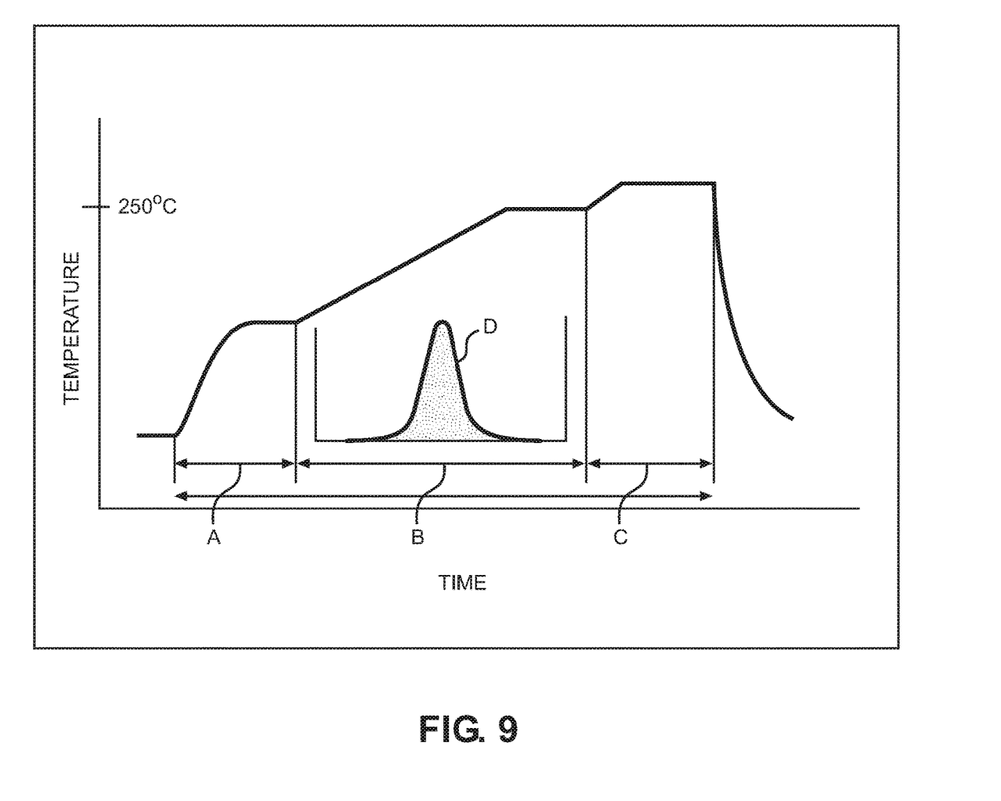
FIG. 9 illustrates a time-temperature profile, according to which a thermoluminescence dosimeter (TLD) sample element may be heated in determining a radiation dose to which that sample element was exposed.

FIG. 9 illustrates a representative time-temperature profile, to which the sample platform (e.g., thermoluminescence dosimetry card), and particularly the suspended or held sample element(s), are subjected, in a card reader to determine a radiation dose to the sample element(s). As shown, the time-temperature profile may include a maximum temperature of at least about 150° C., for example a maximum temperature from about 150° C. to about 300° C. This profile, according to particular embodiments, may include a preheat period A, an emitted radiation acquisition period B, and an annealing period C. The intensity of electromagnetic radiation, such as visible light or near ultraviolet light, may be measured during acquisition period B, and the measured intensity, according to the area under glow curve D, may be correlated with a radiation dose received by sample element(s). Annealing period C at an elevated temperature, i.e., above temperatures to which sample element(s) are subjected during acquisition period B, may be useful for ensuring that the signal to the sample element(s) of the sample platform (e.g., TLD card) is completely removed, such that it can be reused.

EXAMPLES

The following examples are set forth as representative of the present invention. These examples are not to be construed as limiting the scope of the invention as these and other equivalent embodiments will be apparent in view of the present disclosure and appended claims.

Mechanical or manual creasing of the film, for example against a lower corner edge of a top section of a substrate, is effective although not always reproducible in a large-scale manufacturing environment. More robust ways to achieve the same or a similar creasing effect were therefore sought. To this end, the sample platform substrate was altered to effectively impart a mechanical creasing that was previously done by hand. In particular, an angled extension element was added to the bottom plate of this substrate, which resulted in an even higher success rate, approaching 100%, at reducing opportunities for twisting and downward movement of the sample element. In fact, reproducibility was shown to improve from approximately 14% to below 7%, i.e., a two-fold improvement, when "twisting" and "down" movements of sample elements were prevented from occurring.

The tables below provide observed results from conventional sample platforms made in the standard way, i.e., "Conventional A-Plates" (FIG. 1), compared to the sample platforms in which the bottom or second substrate plate was modified to include a creasing "lip" or angled extension element as described above, i.e., "Inventive A-Plates" (FIG. 3). In the data tables below, it is assumed that the sample moves up upon heating, as "up" is the predominant mode. Therefore, any record mark, namely "T" for twisting or "D" for down, is problematic. The tables below represent 720 observations. As is apparent from these tables, the Inventive A-Plates completely eliminated any twisting or down movements of the sample elements.

Conventional A-Plates

|      | i | ii | iii | iv |
|------|---|----|-----|----|
| 1001 |   |    |     |    |
| 1002 |   |    |     |    |
| 1003 |   |    |     | T  |
| 1004 |   |    |     |    |
| 1005 | T |    |     |    |
| 1006 |   | T  |     |    |
| 1007 |   | T  |     |    |
| 1008 |   |    |     |    |
| 1009 |   |    |     |    |
| 1010 |   | T  |     |    |
| 1011 |   |    |     |    |
| 1012 |   | T  |     |    |
| 1013 |   | T  |     |    |
| 1014 |   |    |     |    |
| 1015 |   |    |     |    |
| 1016 |   | T  |     |    |
| 1017 | T |    |     |    |
| 1018 |   |    |     |    |
| 1019 |   |    |     |    |
| 1020 |   |    |     |    |
| 1021 |   |    |     |    |
| 1022 |   |    |     |    |
| 1023 |   |    |     |    |
| 1024 |   |    | T   |    |
| 1025 |   |    |     |    |
| 1026 |   |    |     |    |
| 1027 |   |    |     |    |
| 1028 | T | T  |     |    |
| 1029 |   |    |     |    |
| 1030 | T |    |     |    |
| 1031 |   |    |     |    |
| 1032 |   |    |     |    |
| 1033 |   |    |     |    |
| 1034 |   |    | T   |    |
| 1035 |   |    |     |    |
| 1036 |   |    |     |    |
| 1037 |   |    |     |    |
| 1038 |   |    |     |    |
| 1039 |   |    |     |    |
| 1040 |   | T  |     |    |
| 1041 | T |    |     |    |
| 1042 |   |    |     |    |
| 1043 |   |    |     |    |
| 1044 |   | T  |     |    |
| 1045 |   |    |     |    |
| 1046 |   | T  |     |    |
| 1047 |   |    |     |    |
| 1048 |   |    |     |    |
| 1049 |   | T  |     | T  |
| 1050 |   | T  | T   |    |
| 1051 |   |    |     |    |
| 1052 |   |    | T   |    |
| 1053 |   |    | T   |    |
| 1054 |   | D  |     |    |
| 1055 |   |    | T   |    |
| 1056 |   |    |     |    |
| 1057 |   |    |     |    |
| 1058 |   |    |     |    |
| 1059 |   |    | T   |    |
| 1060 |   |    |     |    |
| 1061 |   |    | T   |    |
| 1062 | T |    |     | T  |
| 1063 |   |    |     |    |

-continued

| | i | ii | iii | iv |
|---|---|---|---|---|
| 1064 | | | | |
| 1065 | | | | |
| 1066 | | | | |
| 1067 | T | | | |
| 1068 | | | | D |
| 1069 | T | | | |
| 1070 | | | | |
| 1071 | | | | |
| 1072 | | | | |
| 1073 | | | | |
| 1074 | | | | |
| 1075 | | | | |
| 1076 | | | | |
| 1077 | | | | |
| 1078 | T | | | |
| 1079 | | | | |
| 1080 | | | | |
| 1081 | | | | |
| 1082 | | | | |
| 1083 | | | T | |
| 1084 | | T | T | |
| 1085 | | | | |
| 1086 | | T | | |
| 1087 | | T | | |
| 1088 | | | | |
| 1089 | | | | |
| 1090 | | | T | |
| 1091 | | | | |

Inventive A-Plates

| | i | ii | iii | iv |
|---|---|---|---|---|
| 1100 | | | | |
| 1101 | | | | |
| 1102 | | | | |
| 1103 | | | | |
| 1104 | | | | |
| 1105 | | | | |
| 1106 | | | | |
| 1107 | | | | |
| 1108 | | | | |
| 1109 | | | | |
| 1110 | | | | |
| 1111 | | | | |
| 1112 | | | | |
| 1113 | | | | |
| 1114 | | | | |
| 1115 | | | | |
| 1116 | | | | |
| 1117 | | | | |
| 1118 | | | | |
| 1119 | | | | |
| 1120 | | | | |
| 1121 | | | | |
| 1122 | | | | |
| 1123 | | | | |
| 1124 | | | | |
| 1125 | | | | |
| 1126 | | | | |
| 1127 | | | | |
| 1128 | | | | |
| 1129 | | | | |
| 1130 | | | | |
| 1131 | | | | |
| 1132 | | | | |
| 1133 | | | | |
| 1134 | | | | |
| 1135 | | | | |
| 1136 | | | | |
| 1137 | | | | |
| 1138 | | | | |
| 1139 | | | | |
| 1140 | | | | |
| 1141 | | | | |
| 1142 | | | | |
| 1143 | | | | |
| 1144 | | | | |
| 1145 | | | | |
| 1146 | | | | |
| 1147 | | | | |
| 1148 | | | | |
| 1149 | | | | |
| 1150 | | | | |
| 1151 | | | | |
| 1152 | | | | |
| 1153 | | | | |
| 1154 | | | | |
| 1155 | | | | |
| 1156 | | | | |
| 1157 | | | | |
| 1158 | | | | |
| 1159 | | | | |
| 1160 | | | | |
| 1161 | | | | |
| 1162 | | | | |
| 1163 | | | | |
| 1164 | | | | |
| 1165 | | | | |
| 1166 | | | | |
| 1167 | | | | |
| 1168 | | | | |
| 1169 | | | | |
| 1170 | | | | |
| 1171 | | | | |
| 1172 | | | | |
| 1173 | | | | |
| 1174 | | | | |
| 1175 | | | | |
| 1176 | | | | |
| 1177 | | | | |
| 1178 | | | | |
| 1179 | | | | |
| 1180 | | | | |
| 1181 | | | | |
| 1182 | | | | |
| 1183 | | | | |
| 1184 | | | | |
| 1185 | | | | |
| 1186 | | | | |
| 1187 | | | | |
| 1188 | | | | |
| 1189 | | | | |
| 1190 | | | | |

Overall, aspects of the invention are directed to substrates for suspending or holding (e.g., encapsulating) sample elements, sample platforms (e.g., TLD cards), methods for making such platforms, and methods for determining a radiation dose, all of which may be associated with improvements in positional stability of sample elements, as well as with overall reproducibility of radiation dose measurements. Such improvements may reside in the tensioning of films used to suspend or hold such sample elements, according to embodiments as described herein. Those having skill in the art, with the knowledge gained from the present disclosure, will recognize that various changes can be made to the disclosed devices and methods in attaining these and other advantages, without departing from the scope of the present invention. Accordingly, it should be understood that the features described herein are susceptible to changes or substitutions. The specific embodiments illustrated and described herein are for illustrative purposes only, and not limiting of the invention as set forth in the appended claims.

What is claimed is:

1. A substrate for suspending a sample element, the substrate comprising top and bottom sections that are configured, upon alignment, to form a substrate opening and engage an outer region of a film that is external to a central region extending across the opening;
   wherein the top and bottom sections are further configured to mechanically tension the central region of film across the opening by displacement of the film along an edge of the opening formed in part by an extension element of the bottom section that is angled in a direction that is offset from a plane of the opening, and wherein the alignment of the top and bottom sections provides a chamfer in the opening.

2. A sample platform comprising:
   a substrate having a plurality of openings across each of which a central region of a film extends, and
   a plurality of sample elements each suspended by the central region of the film within one of the openings,
   wherein each of the central regions of the film is tensioned across the respective opening to reduce movement of the respective sample element upon heating.

3. The sample platform of claim 2, wherein the substrate comprises four openings and the sample platform comprises four sample elements, each sample element comprising a different thermoluminescent material type or material mass density for measuring differing types of ionizing radiation.

4. The sample platform of claim 2, wherein each of the central regions of the film is tensioned across the respective opening by displacement of the film in a direction that is offset from a plane of the respective opening.

5. The sample platform of claim 4, wherein the displacement occurs along an edge of the respective opening.

6. The sample platform of claim 5, wherein the displacement results from a crease in the film at the edge of the respective opening.

7. The sample platform of claim 6, wherein the crease is formed upon alignment of a top section of the substrate with a bottom section of the substrate having an extension element.

8. The sample platform of claim 1, wherein the opening is circular.

9. The sample platform of claim 8, wherein the opening has a diameter from about 5 millimeters (mm) to about 30 mm.

10. A method for determining a radiation dose, the method comprising:
    reading a sample element of a sample platform by exposure of the sample element to heat or light, and
    measuring the intensity of electromagnetic radiation emitted by the sample element;
    wherein the sample platform comprises a substrate comprising top and bottom sections that are configured, upon alignment, to form a substrate opening and engage an outer region of a film that is external to a central region extending across the opening;
    wherein the top and bottom sections are further configured to mechanically tension the central region of film across the opening.

11. The method of claim 10, wherein movement of the sample element during the reading is reduced, relative to a reference method in which the central region of the film is not tensioned.

12. The method of claim 11, wherein the movement of the sample element that is reduced is a downward movement or a twisting movement.

13. The method of claim 10, wherein the reading of the sample element is by exposure of the sample element to heat, according to a time-temperature profile.

14. The method of claim 13, wherein the time-temperature profile includes a maximum temperature of at least about 150° C.

15. The method of claim 10, wherein the reading of the sample element is by exposure of the sample element to light, wherein the light has a first wavelength that differs from a second wavelength of the electromagnetic radiation emitted by the sample element.

16. A method of making a dosimetry card, the method comprising:
    affixing an outer region of a film to a first plate of a substrate, in a manner such that a central region of the film, which supports a sample element, extends across a first plate opening;
    aligning a second plate opening of a second plate with the first plate opening to form a substrate opening;
    wherein the film is tensioned across the substrate opening by creasing the film at an edge of the substrate opening and the dosimetry card is a thermoluminescence dosimetry (TLD) card or an optically stimulated luminescence dosimetry (OSLD) card.

17. The method of claim 16, wherein the film is tensioned by creasing the film against the first plate of the substrate, prior to the aligning of the second plate opening with the first plate opening.

18. The method of claim 16, wherein the creasing is performed upon the aligning of the second plate, by an extension element of the second plate that protrudes radially inward, to a greater extent relative to the first plate opening.

* * * * *